(12) United States Patent
Sabel

(10) Patent No.: US 7,367,671 B2
(45) Date of Patent: May 6, 2008

(54) PROCESS AND DEVICE FOR THE TRAINING OF HUMAN VISION

(75) Inventor: Bernhard Sabel, Berlin (DE)

(73) Assignee: NovaVision, Inc., Boca Raton, FL (US)

( * ) Notice: Subject to any disclaimer, the term of this patent is extended or adjusted under 35 U.S.C. 154(b) by 250 days.

(21) Appl. No.: 10/503,869

(22) PCT Filed: Feb. 8, 2002

(86) PCT No.: PCT/EP02/01339

§ 371 (c)(1),
(2), (4) Date: May 18, 2005

(87) PCT Pub. No.: WO03/065964

PCT Pub. Date: Aug. 14, 2003

(65) Prior Publication Data

US 2005/0213033 A1     Sep. 29, 2005

(51) Int. Cl.
*A61B 3/00* (2006.01)
(52) U.S. Cl. .................................... 351/203
(58) Field of Classification Search ............... 351/203, 351/205, 206, 208, 210, 212, 214, 216, 220, 351/222, 200, 246
See application file for complete search history.

(56) References Cited

U.S. PATENT DOCUMENTS 2,213,484 A    9/1940   Briggs .................. 128/76.5

(Continued)

FOREIGN PATENT DOCUMENTS

| DE | 9305147 | 8/1994 |
|----|---------|--------|
| EP | 115263  | 12/1983 |
| EP | 128783  | 3/1984 |

(Continued)

OTHER PUBLICATIONS

Alan Cowley, Perimetric Study of Field Defects in Monkeys After Cortical and Retinal Ablations, Quarterly Journal of Experimental Psychology, pp. 232-245, Dec. 18, 1967.

(Continued)

*Primary Examiner*—Ricky Mack
*Assistant Examiner*—Tuyen Tra
(74) *Attorney, Agent, or Firm*—Bromberg & Sunstein LLP

(57) ABSTRACT

The present invention relates to a process for training the visual system of a human by presenting optical stimuli to said human, said stimuli being presented to a zone within the intact visual field of said human and optionally to a zone outside the intact visual field of said human, one of said zones comprising a zone to be trained, thereby allowing an improvement of the vision in general, said process comprising the steps of (a) locating and defining a zone of intact vision and optionally a zone of deteriorated vision or residual visual function or partial visual system injury ("transition zone") within the human's visual system; (b) defining a training area which is located within at least one of said zones including the zone of intact vision; (c) training the human's visual system by presenting visual stimuli to the human's visual system, at least a part of said visual stimuli being presented in or near said zone of intact vision; (d) recording changes in the characteristics of the human's visual system; (e) adapting the location and definition of the stimulus presentation to said at least one zone, including the zone of intact vision, according to said changes; and (f) reiterating the previous steps continuously so as to improve the human's overall visual system. The invention also relates to a device for performing said process.

37 Claims, 5 Drawing Sheets

Figure 1:
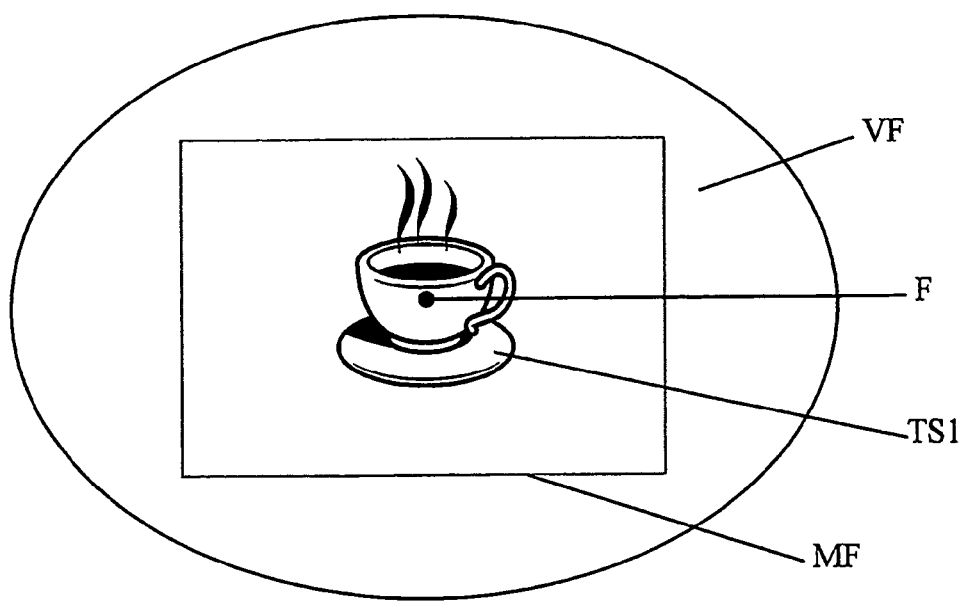

F = Fixation Point
TS1 = Target Stimulus 1
VF = Visual Field
MF = Monitor frame

U.S. PATENT DOCUMENTS

| | | | |
|---|---|---|---|
| 4,260,227 A | 4/1981 | Munnerlyn et al. | 351/24 |
| 4,408,846 A | 10/1983 | Balliet | 351/203 |
| 4,429,961 A | 2/1984 | Sheingorn | 351/226 |
| 4,533,221 A | 8/1985 | Trachtman | 351/203 |
| 4,660,945 A | 4/1987 | Trachtman | 351/203 |
| 4,679,920 A | 7/1987 | Takashi et al. | 351/226 |
| 4,971,434 A | 11/1990 | Ball | 351/224 |
| 5,050,982 A | 9/1991 | Meissner | 351/203 |
| 5,088,810 A | 2/1992 | Galanter et al. | 351/203 |
| 5,191,367 A | 3/1993 | Salibello et al. | 351/243 |
| 5,206,671 A | 4/1993 | Eydelman et al. | 351/203 |
| 5,241,332 A | 8/1993 | Farrell | 351/246 |
| 5,305,027 A | 4/1994 | Patterson | 351/44 |
| 5,321,445 A | 6/1994 | Fossetti | 351/203 |
| 5,325,136 A | 6/1994 | Salibello et al. | 351/243 |
| 5,363,154 A | 11/1994 | Galanter et al. | 351/203 |
| 5,455,643 A | 10/1995 | Ki-Ho | 351/203 |
| 5,534,953 A | 7/1996 | Schmielau | 351/203 |
| 5,539,481 A | 7/1996 | Vax | 351/203 |
| 5,550,602 A | 8/1996 | Braeuning | 351/203 |
| 5,946,075 A | 8/1999 | Horn | 351/246 |
| 5,991,085 A | 11/1999 | Rallison et al. | 359/630 |
| 6,062,687 A | 5/2000 | Lofgren-Nisser | 351/46 |
| 6,321,338 B1 | 11/2001 | Porras et al. | 713/201 |
| 6,359,601 B1 | 3/2002 | Maguire, Jr. | 345/7 |
| 6,364,486 B1 | 4/2002 | Ball et al. | 351/203 |
| 6,386,706 B1 | 5/2002 | McClure et al. | 351/203 |
| 6,406,437 B1 | 6/2002 | Zur et al. | 600/558 |
| 6,431,708 B2 | 8/2002 | Krebs | 351/203 |
| 6,443,977 B1 | 9/2002 | Jaillet | 607/88 |
| 6,464,356 B1 * | 10/2002 | Sabel et al. | 351/203 |
| 6,519,703 B1 | 2/2003 | Joyce | 713/201 |
| 6,540,355 B1 | 4/2003 | Couture | 351/203 |
| 6,592,221 B1 | 7/2003 | Stregova | 351/237 |
| 7,004,912 B2 | 2/2006 | Polat | 600/558 |
| 2002/0047987 A1 | 4/2002 | Massengill et al. | 351/204 |
| 2002/0107960 A1 | 8/2002 | Wetherall et al. | 709/225 |
| 2003/0156254 A1 | 8/2003 | Turovetsky | 351/203 |
| 2004/0051848 A1 | 3/2004 | Gotze et al. | 351/203 |
| 2004/0100616 A1 | 5/2004 | Eremeev | 351/203 |

FOREIGN PATENT DOCUMENTS

| | | |
|---|---|---|
| EP | 135736 | 8/1984 |
| EP | 0242723 | 4/1987 |
| EP | 0537945 A1 | 10/1992 |
| EP | 544631 | 11/1992 |
| EP | 689822 | 7/1994 |
| EP | 775464 | 11/1995 |
| EP | 830839 | 9/1997 |
| EP | 1236433 | 3/2001 |
| EP | 1402869 | 12/2001 |
| EP | 1 236 432 | 9/2002 |
| EP | 1403680 A1 | 8/2003 |
| GB | 1465561 | 2/1977 |
| WO | WO 8000405 | 8/1979 |
| WO | WO 8810088 | 6/1988 |
| WO | WO 9100553 | 6/1990 |
| WO | WO 9110393 | 1/1991 |
| WO | WO 9200037 | 6/1991 |
| WO | WO 9517227 | 12/1994 |
| WO | WO 9811819 | 3/1998 |
| WO | WO 9849992 | 5/1998 |
| WO | WO 9959461 | 12/1998 |
| WO | WO 9952419 | 4/1999 |
| WO | WO 0036971 | 12/1999 |
| WO | WO 00/12042 | 3/2000 |
| WO | WO 0180808 | 4/2000 |
| WO | WO 0113859 | 7/2000 |
| WO | WO 0145630 | 12/2000 |
| WO | WO 0147463 | 12/2000 |
| WO | WO 02053072 | 7/2002 |
| WO | WO 03002070 | 1/2003 |
| WO | WO 03002190 | 1/2003 |
| WO | WO 03007944 | 1/2003 |
| WO | WO 03020195 | 3/2003 |
| WO | WO 03041630 | 5/2003 |

OTHER PUBLICATIONS

J. Zihl, Zur Behandlung von Patienten mit homonymen Gesichtsfeldstorungen. (Treatment of patients with homonymous visual field disorders), Zeitschrift fur Neuropsychologic, vol. 2, pp. 95-101, 1990.

Erich Kasten, Bernhard A. Sabel, Visual field enlargement after computer training in brain-damaged patients with homonymous deficits: an open pilot trial, Restorative Neurology and Neuroscience vol. 8, pp. 113-127, 1995.

International Preliminary Examination Report, Dec. 18, 2003.

Patienteninformation Sehtherapie, Spectros, Nethera, http://www.teltra.org/cms/site/index.php?id=13, Apr. 6, 2005.

Patienteninformation Sehtherapie, Otcb, Nethera, http://www.teltra.org/cms/site/index.php?id=80, Apr. 6, 2005.

Spectros Technik/Ablauf, Nethera, Teltra, http://www.teltra.org/cms/site/index.php?id=77, Apr. 5, 2005.

Erich Kasten et al., Computer-based training for the treatment of partial blindness, Nature Medicine, vol. 4, No. 9, p. 1083-1087, Sep. 1998.

Burkhard Pleger et al., Functional magnetic resonance imaging mirrors recovery of visual perception after repetitive tachistoscopic stimulation in patients with partial cortical blindness, Neuroscience Letters, vol. 335, p. 192-194, 2003.

Walter Widdig et al., Repetitive visual stimulation: A neuropsychological approach to the treatment of cortical blindness, NeuroRehabilitation, vol. 18, p. 227-237, 2003.

Robert Sekuler, Vision Loss in an Aging Society: A Multidisciplinary Perspective/Vision Rehabilitation: Assessment, Intervention and Outcomes/The Lighthouse Handbook on Vision; Aug. 1, 2001, Gerontologist 556, vol. 41, Issue 4; ISSN: 0016-9013, © 2001.

Erich Kasten, Dorothe A. Poggel, Bernhard A. Sabel, Computer Based Training Stimulus Detection Improves Color and Simple Pattern Recognition in the Defective Field of Hemianopic Subjects; Nov. 1, 2000, Journal of Cognitive Neuroscience 1001, ISSN: 0898-929X; vol. 12, Issue 6; © 2000.

Rewiring Your Gray Matter: The brain: You can trach an old brain new tricks. Neuroplasticity promises to give a whole new meaning to 'changing your mind'; Jan. 1, 2000, Newsweek 63; ISSN: 0028-9604; vol. 134, Issue 26, © 2000.

Teaching the brain to restore sight; Popular Mechanics, Jan. 18, 1999, Associated Press Newswires, © 1999.

Philip A. Schwartzkroin, Synaptic Plasticity: Molecular, Cellular, and Functional Aspects (book reviews); May 20, 1994, Science 1179; vol. 264, No. 5162, ISSN: 0036-8075; © 1994.

J. Zihl, et al., Restitution of visual function in patients with cerebral blindness; Zihl and von Cramon, J Neurol Neurosurg Psychiatry (1979).

J. Zihl, et al., Restitution of visual field in patients with damage to the geniculostriate visual pathway; Zihl and von Cramon, Human Neurobiology (1982).

E. Kasten, S. Wuest, B. Sabel, Journal of Clinical and Experimental Neuropsychology 1998, vol. 20, No. 5, pp. 581-598 "Residual Vision in Transition Zones in Patients with Cerebral Blindness".

F. Schmielau, Restitution of visual function in cases of brain damaged patients: Efficacy of localization specific sensory and sensomotoric rehabilitation procedures. In "Psychologie in der Neurologie" [Psychology in Neurology], P. Jacobi (editor). Berlin: Springer, 115-126(1989).

E. Kasten et al., Restoration of vision II: Residual functions and training-induced visual field enlargement in brain-damaged patients.

K.K. Ball, et al, Journal of the Optical Society of America A, vol. 5, No. 12, pp. 2210-2219 "Age and Visual Search: Expanding the Useful Field of View", Dec. 1998.

E. Kasten, et al., Spatial Vision, vol. 10, No. 4, pp. 499-503, "Programs for Diagnosis and Therapy of Visual Field Deficits in Vision Rehabilitation", 1997.

W. Widdig et al., Repetitive visual stimulation: A neuropsychological approach to the treatment of cortical blindness, Neuro. Rehabilitation 18 (2003) 227-237.

W. Widdig et al., Functional magnetic resonance imaging mirrors recovery of visual perception after repetitive tachistoscopic stimulation in patients with partial cortical blindness, Neuroscience Letters 335 (2003) 192-196).

* cited by examiner

F = Fixation Point
TS1 = Target Stimulus 1
VF = Visual Field
MF = Monitor frame

VF = Visual Field
MF = Monitor Frame
B = Blind Region
TZ = Transition Zone
TS1 = Target Stimulus 1
TS2 = Target Stimulus 2
F = Fixation Point
I = Intact Visual Field Sector I = Intact Visual Field Sector
FA = Fixation Ankers
MF = Monitor Frame
B = Blind Region
TS1 = Letters or Words as Target Stimuli
VF = Visual Field

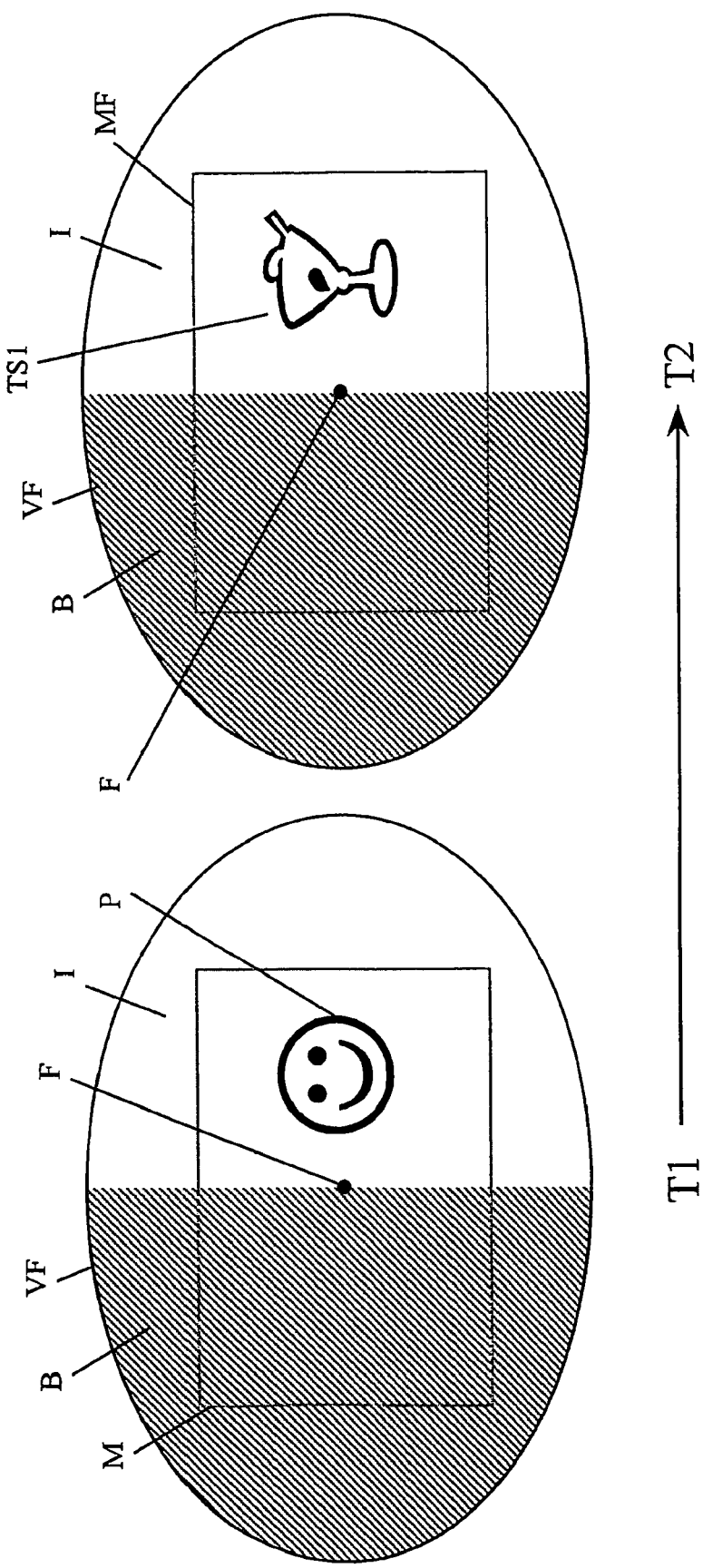

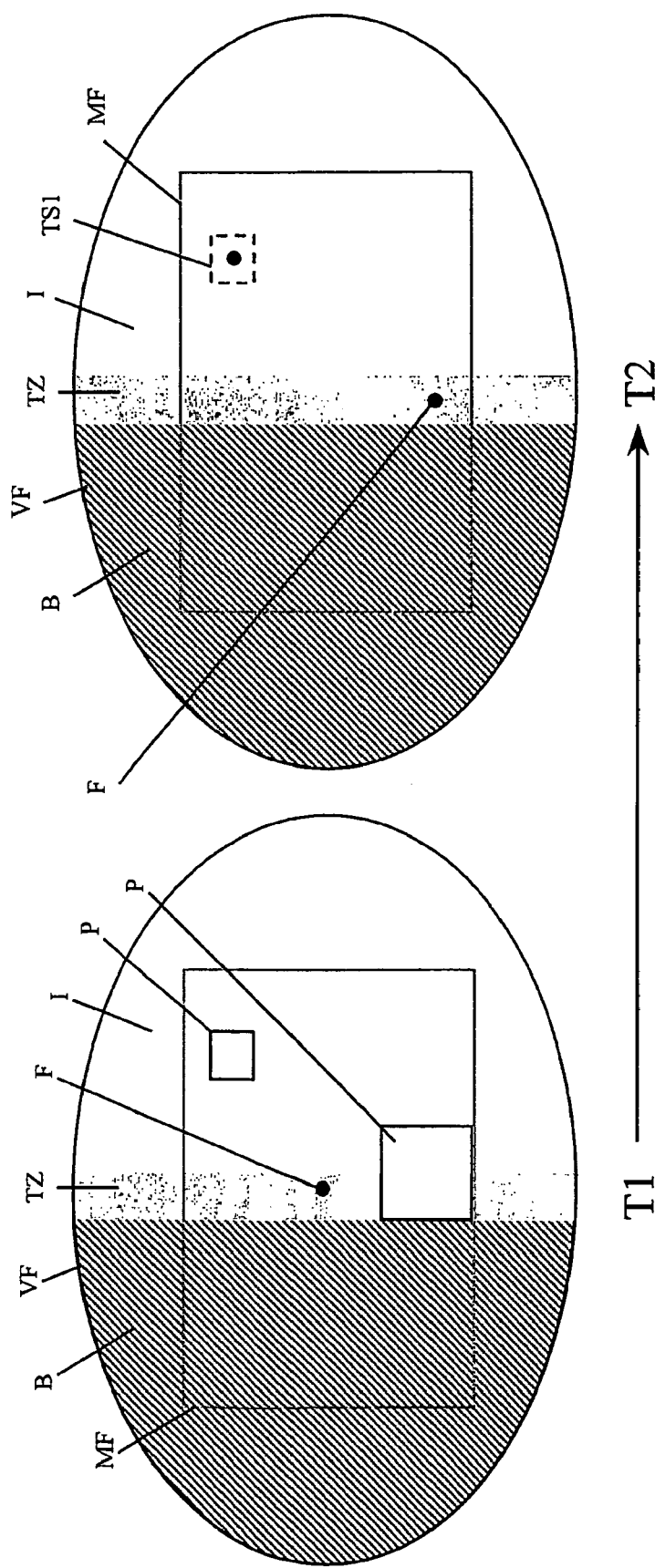

PROCESS AND DEVICE FOR THE TRAINING OF HUMAN VISION

The present invention concerns an improved process and device for the training of human vision. In particular, the invention relates to a process and apparatus by which a change of the visual performance of persons in need of a training for improvement or completion of their vision can be affected by stimulating their visual system with optical stimuli.

A damage to the visual system is, for the purposes of the present invention, defined in the present specification and claims, as a damage of any structure (or of all structures) involved in the processing of vision. These structures include, but are not restricted to the nervous system tissue from the level of the retina up to the optic nerve and all brain structures involved. Such a damage leads to deficits or even a loss of visual functions which may result into partial or more or less complete blindness.

Impairments of a human's visual system may either result from an incomplete or impaired development of the visual system during infancy or from a deterioration either continuously and naturally due to ageing of the person or more or less abruptly due to diseases or accidents more or less severely influencing the visual system. It was, for example, found that the vision of children can substantially be improved by regular sessions of training their visual system, e.g. in cases of squinting. On the other hand, persons whose vision was deteriorated for any reason may either stop the deteriorating development or even improve their vision by a specific training adapted to the cause of deterioration of their visual system. The present invention intends to provide an improved process and device for training and improving a human's vision in all conceivable cases of impairment where the presentation of optical stimuli to the visual system of a person having need for an improvement of the vision may promise a successful removal of the cause of impairment and/or increase his/her performance.

In recent years computer-technology has been utilized to train mental functions of the human brain. For example, the prior art reports on methods to treat temporal processing deficits of language-learning impaired children using computer-training as a paradigm. It is not clear, however, whether computer-based training can facilitate other sensory modalities such as visual functions after a damage to the brain.

Brain injury, which may result from stroke or trauma, often impairs visual functions. Persons typically loose sight in one half of the visual field while the other side often remains unimpaired. This partial blindness was, for a long time, considered untreatable because it was the long-held belief that proper vision requires a highly specific neuronal organization. Despite this specificity in neuronal organization, there is, however, a considerable degree of plasticity in the injured visual system. Lost visual functions can recover spontaneously to some extent in animals and man. At least some of this spontaneous post-lesion neuroplasticity of the adult visual system is due to extensive receptive field reorganization following lesions in retina or cortex.

In the prior art, training methods have been disclosed that can be used to improve visual functions of brain damaged monkeys (A. Cowey, Perimetric study of field defects in monkeys after cortical and retinal ablations, Quart. J. Exp. Psychol. 19, 232-245 (1967)) and of men (J. Zihl, Zur Behandlung von Personen mit homonymen Gesichtsfeldstörungen, Z. Neuropsychol. 2, 95-101 (1990); E. Kasten, B. A. Sabel, Visual field enlargement after computer training in brain damaged persons with homonymous deficits: an open pilot trial, Restor. Neurol. Neurosci. 8, 113-127 (1995)). Several observations were made that suggest that humans with visual system damage may benefit from visual training.

The first observation that visual training may be effective in humans is the study by Zihl et al. (loc. cit.), who found that repeated presentation of visual stimuli and measurements of incremental thresholds at the border to the blind field in the same retinal location results in small expansions of visual field borders in persons with visual field defects. Repeated testing in this situation requires, however, an experimenter to carry out the training with the person to be trained, i.e. this method cannot be used by the person independently. Thus, it is extremely time consuming for both the person and the experimenter.

In the document No. DE-U 93 05 147 issued to Schmielau, a device for training the visual system of humans is described consisting of a large size hemispheric half bowl. Here, arrays of small light bulbs are positioned in a large diameter semicircle. Light stimuli are presented by illuminating sequences of said light bulbs arranged closely to each other such that they may stimulate the visual field in different excentricities from the center which has to be visually fixed. While this device does allow assessment and training of the entire visual field in its full extent, it has several disadvantages which preclude its widespread use. The disadvantages are (1) its size, (2) the inflexible position with which visual stimuli can be presented, and (3) the absence of any teaching of orienting the training according to the residual visual functions. Due to the lack of presentation strategy, the use of the Schmielau prior art device requires extended time periods. In addition, the half bowl used for training is inpracticable for home use.

The limitation of the Schmielau invention is apparent from the FIG. 4 of said document: There, as also described in classical text books, the whole visual system of a human is shown by areas which are either intact or deficient. There is no mention of areas of impaired, residual visual functions based on which a visual field training may be performed.

One may presume that computers might be useful to replace such a large size, unpracticable device, but Schmielau (loc. cit.) states that this is not possible. Therefore, since it is clearly stated that computer controlled training is not useful for purposes of visual field training, the use of computers was always refused in the prior art by those skilled in the art.

It was already found in the prior art referred to above that a computer-controlled training procedure for visual functions of a human can contribute considerably to an improvement of the training effect. There was, therefore, developed a computer program which has been described elsewhere (E. Kasten, B. A. Sabel, Visual field enlargement after computer training in brain damaged persons with homonymous deficits: an open pilot trial. Restor. Neurol. Neurosci. 8, 113-127 (1995)). The principle advantage of using a computer-controlled device is that it is much smaller and that it allows the continuous recording of the person's performance. However, the programs described by Kasten et al. (loc. cit.) present the stimuli in random order on a computer screen, without considering the person's actual performance in the visual task. Therefore, training has been time consuming and inefficient, though this method has been shown effective in an early pilot study.

In the paper published by Kasten et al. (1997; loc. cit.) a program has been described. "Sehtra", for instance, presents small light stimuli of variable luminance in all parts of the visual field, but it does not adapt to the person's actual performance in the different field sectors. It is noted that the stimuli are presented at random by a predetermined sector of the monitor to the person's visual field, without considering the actual nature of the deficit and the zone of partial visual system injury or residual visual function (so-called "transition zone").

In order to overcome this limitation, there was described a process and device for the training of human vision, which avoid the known disadvantages, in the document WO 00/12042. The process and device for the training of human vision described in said document take into account the training of zones of the person's visual system where residual visual functions are maintained or where the natural vision is partly deteriorated only or where the natural vision is to be maintained on a high quality level (so-called "transition zones"). It was found that the training of the human visual system in such a transition zone allows an extension of the person's visual field from an intact zone into said transition zone and from said transition zone into a zone of substantially complete visual system injury in the case that the vision of a person is severely injured. The process and device provided in accordance with the proposal in said document provide a process and a device for the training of a human's vision which may be handled not only in usual training centers under the supervision of an experienced experimenter but also in the person's private environment by himself/herself.

As a result of the development in the prior art, skilled people were taught methods to enlarge the visual field using training procedures and, thus, help patients to restore some of the visual functions. This was achieved by establishing, through diagnostic testing using visual stimulation, borders between the intact and the damaged visual field and defining areas of residual vision using computer-based high resolution visual field testing. The areas of residual vision or transition zones were then stimulated by a training procedure, whereby the vision could be improved.

In the course of further research, it was surprisingly found that the training procedure sometimes leads to improvements of vision as subjectively reported by the persons trained, even though the position of the border does not change. This suggests that improvements of the vision must have occurred in the intact part of the visual field, i.e. that areas which appear to be intact, without visual deficits, must have improved their function to some degree.

Thus, in the search for methods for the treatment of visual defects, treatment of the apparent deficit region alone, i.e. the blind field and the transition zone, is not the only method to help restore visual functions after visual system damage. Rather, it is now proposed and was found that a training in the presumedly intact regions of the visual field with or without a training of the transition zones can improve visual capabilities in patients having a damaged visual system.

It was, hence, an object of the present invention to make, with persons to be trained, even more use of the visual capabilities which are left after a damage to the visual system of said persons, for example after a brain injury. It was a further object of the present invention to provide an apparatus allowing the stimulation, by optical stimuli, of the intact brain region(s) and optionally also of the damaged brain region(s).

Surprisingly, the above objects were achieved by the present invention. The inventors conceived a new manner by which visual stimuli are presented on a simple device for emitting optical stimuli to the visual system of a human in such a way that target stimuli (by which a person to be trained can perform training) are presented to the intact sector of the visual field, optionally together with a presentation of optical stimuli to the partly damaged sector.

In a very general sense, the invention relates to a process for training the visual system of a human by presenting optical stimuli to said human, said stimuli being presented to a zone within the intact visual field of said human and optionally to a zone outside the intact visual field of said human, one of said zones comprising a zone to be trained, thereby allowing an improvement of the vision in general, said process comprising the steps of locating and defining a zone of intact vision and optionally a zone of deteriorated vision or residual visual function or partial visual system injury ("transition zone") within the human's visual system;

defining a training area which is located within at least one of said zones including the zone of intact vision;

training the human's visual system by presenting visual stimuli to the human's visual system, at least a part of said visual stimuli being presented in or near said zone of intact vision;

recording changes in the characteristics of the human's visual system;

adapting the location and definition of the stimulus presentation to said at least one zone, including the zone of intact vision, according to said changes; and reiterating the previous steps continuously so as to improve the human's overall visual system.

In a further embodiment, the invention relates to a device for training the visual system or vision of a human allowing the above training process to be conducted. The device essentially comprises a central data processing means for recording, storing, processing and emitting data from the other means of the device;

at least one optical stimuli presenting means;

a fixation point means allowing the fixation of the person's view;

means for entering the person's response on optical stimuli perceived;

means for allowing a control of said at least one optical stimuli presenting means in accordance with the performance of the person responding on optical stimuli perceived.

In a preferred embodiment of the invention, said device enables the steps of locating and defining a zone of intact vision and optionally a zone of deteriorated vision or residual visual function or partial visual system injury ("transition zone") within the human's visual system;

defining a training area which is located within at least one of said zones including the zone of intact vision;

training the human's visual system by presenting visual stimuli to the human's visual system, at least a part of said visual stimuli being presented in or near said zone of intact vision;

recording changes in the characteristics of the human's visual system;

adapting the location and definition of the stimulus presentation to said at least one zone, including the zone of intact vision, according to said changes; and reiterating the previous steps continuously so as to improve the human's overall visual system.

Thus, the inherent feature of the present invention is that the training by stimulus presentation predominantly occurs in or near the zone of intact vision, but optionally also in the zone of deteriorated vision or in the zone of residual visual function or in the zone of partial visual system injury, i.e. in the transition zone. Hence, in contrast to the teachings of the prior art, the training, by presenting visual stimuli, occurs preferably only in the zone of intact vision, although a parallel or consecutive presentation of optical stimuli to at least one other zone, e.g. to the so-called "transition zone" may occur, in addition to the presentation of stimuli to the zone of intact vision. In other words: If only one zone is to be trained, this is, in accordance with the present invention, the zone of intact vision of the human to be trained. Thereby, the human's vision can be improved much more efficiently than in the prior art.

The term "zone of intact vision" as defined in connection with the present description of the invention and the claims means the zone of the visual field (or brain area) which is substantially not injured or influenced by the events resulting into an impairment of the visual system, i.e. shows more or less normal visual performance when receiving optical stimuli. In contrast, the term "zone of deteriorated vision" (which is used in a similar sense as the term "zone of residual visual function" or the term "zone of partial visual system injury") is defined, in connection with the present description of the invention and the claims, to mean the zone where events like accidents or stroke or degenerative diseases caused damages of the brain regions or the retina influencing the visual capabilities of the human so that the vision is at least partly deteriorated or even partly or completely lost.

Zones of intact vision, on the one hand, and zones of deteriorated or even lost vision, on the other hand, may be shaped continuously, i.e. as zones of a certain (e.g. round) shape, wherein the zone of said shape has more or less identical visual capabilities, as, for example intact visual capabilities. Such continuous zones may be adjacent to another (optionally similarly shaped) zone having a different visual capability as, for example, a zone of deteriorated vision, which, in turn, may be followed by a zone where the vision was completely lost. However, it may also be possible, and is considered to be covered by the present invention, that several zones of intact vision are surrounded, in a discontinuous manner, by zones of deteriorated or lost vision. When the visual field is lost, for example, following stroke, a typical regional field loss (such as hemianopsia) occurs. Often, the person having experienced said event can still fixate, and the region of intact vision is in one side of the visual field and comprises a solid field of vision. In the case of macula degeneration diseases or other diseases that result into a loss of fixation of the fovea, there may be a circular visual field that is donut-shaped, with a deficit region in the centre of the visual field (damaging the fovea) and with intact areas surrounding it (see FIG. 3).

Thus, in accordance with the present invention, we developed another approach by concentrating the visual stimulus presentations to those areas of the visual field in which a more efficient rehabilitation progress can be expected, i.e. the intact areas.

To overcome the limitation of the prior art devices, we now propose in accordance with the present invention to first locate, define and characterize the zones of intact vision, instead of (or optionally together with) zones of impaired, i.e. deteriorated vision or residual visual function or partial visual system injury. The zones of deteriorated vision or impaired vision or partial visual system injury are hereinafter shortly referred to as "transition zones" (see FIG. 2), while the zones of intact vision are simply referred to as "zones of intact vision". Such transition zones may, for example, be found with aged people whose vision, for example lateral vision, becomes more and more restricted. Transition zones may also be found with people whose visual system was influenced as a result of a brain injury, stroke or similar event. Another example are transition zones between zones of completely maintained and wholly lost ability to visually discriminate between colours, shapes or movements. However, the predominant training areas or training zones which are defined in the next step of the present procedure are located in the intact vision zones.

In a preferred embodiment of the invention, the size and location of said training area or areas within said intact vision zone(s) are selected in accordance with the size, location and kind of the zone of partial visual system deterioration, of residual visual function or visual deficit of said human. In other words: It has to be checked carefully, which parts of the visual system of said human offer the greatest chance for improving the overall vision by the subsequent training by presenting optical stimuli. In accordance with the present invention, not only (or even less preferred) the transition zones are trained together with the zones of intact vision, but preferably the zone(s) of intact vision alone will receive the training by the presentation of optical stimuli.

Then, based on the individual person's performance which is determined continuously or intermittently during said training, we propose to present the training stimuli in those zones of intact vision. The type, shape, intensity, duration and time sequence of the training stimuli is not restricted; there may be used one type of training stimuli or several types of training stimuli. In the latter case, several types may be used simultaneously or in a time sequence. In preferred embodiments of the invention, optical and—even more preferred—light stimuli are presented to the person's visual system. It is even more preferred that light stimuli of different colour, luminance, intensity and/or shape are presented to the visual system of the person to be trained. Such light stimuli can be presented as static light stimuli or a series of light stimuli in a sequence generating an impression of a moving object. In another embodiment of the invention, stimuli in the form of simple or more differentiated pictures of articles of daily life are presented to the intact vision zone of the person to be trained. Such pictures may be static or moving (dynamic), according to the needs. Another preferred embodiment of the invention comprises the presentation of optical stimuli to the intact vision zone of the person to be trained, which have the form of letters, ciphers or even words or sentences. The invention, however, is not at all restricted to the above preferred embodiments of stimuli to be presented.

Without wanting to be bound by a theory, it is assumed that this "intact-vision-zone based stimulus presentation" is based on the consideration that there are areas of substantially intact vision of a person where vision is almost not deteriorated or completely intact. In these areas, most of the neuronal structures survived the injury. It is reasoned that these surviving neurons, since their number exceeds a certain minimum ("hypothesis of minimal residual structure"), mediate the complete return of vision due to training, and therefore their stimulation by training would be the critical step to be taken. As a consequence, to overcome the previously recognized problems of insufficient visual field stimulation, we therefore devised a new presentation strategy by selectively stimulating these zones of intact vision using a computer-controlled stimulation device.

In a first process step, the person's visual field defect is measured. This includes the step of establishing a zone of intact visual field. The measurement is done by methods which are, as such, known from the prior art. In one embodiment of the invention, standard perimetry devices may be used, i.e. those devices, which are commonly used in the ophthalmological practice. In a preferred embodiment of the invention, a computer-based campimetric measurement is conducted, as for example that one which was described by the inventors. With such a device, blind, partially injured and intact sectors of the visual field can be defined.

The definition of what comprises the border between the intact zone and the partially injured zone or the intact zone and the blind zone may vary. Its position will depend on what kind of stimuli are used to define the visual function, i.e. large or small stimuli, bright or less bright stimuli, etc., the nature of the background, i.e. cluttered or simple backgrounds, and/or the timing of the stimulus, i.e. short or long presentation times.

In the second step, the zone or area of intact vision is defined, based on the measurement of the first step. The definition of the intact visual field depends on the nature of the visual stimulation selected for said definition. Stimuli which are seen more easily by the person to be trained will produce a larger apparent visual field, while stimuli which are responded to less will produce smaller apparent visual fields. Whatever method is selected to define the visual field or intact visual zone, the result of this step is a clear zone or area of vision that is defined to be intact. The shape of the intact visual field is not restricted. It may be one large area, usually round in shape, but may also consist of several intact regions which are not connected to each other.

In the third—and decisive—training step, a sequence of visual stimuli is presented to the intact visual zone of the person to be trained. The task the person to be trained has to perform is to respond, as in the prior art, to the stimulus presentation by a reaction which may be a step of pressing a key or any other input device in order to demonstrate that the stimulus—or a sequence of stimuli—was seen and recognized.

The new feature of the present invention comprises the presentation of the target stimulus to the intact vision zone(s) of the person to be trained, whereby the stimulus is selected from a library of visual objects exemplified above. The transition zone(s), near the border of blindness, may be trained in addition consecutively or may be trained in parallel; however, the aim of the present invention is directed to the primary training of the intact vision zone(s).

As the size and shape and optionally also the number of the intact vision zones may vary, the presentation of the stimuli is adjusted in such a way that the location and size of the objects fits within the boundaries of the intact vision zone(s) according to the above measurements. The target stimulus may be presented, for example, on a computer monitor. It could be any type of a single stimulus, or there may be selected several or many stimuli together or successively with or without different types of background. For example, useful target stimuli could be letters, words, sentences, meaningful objects (drawings, faces, photographs etc.) or objects without meaning (dots, a line pattern etc.) moving or not moving on the screen. As long as the presentation is occurring in the intact vision zone, defined as the position of the field in relation to a fixation point, and as long as the blind zone of the visual field of the person to be trained is not stimulated, any stimulus or combination of stimuli may be used.

By presenting the stimuli in the above-described way to the intact vision zone of the person to be trained, the intact vision zone is trained, and the training steps are repeated for training purposes.

Specific algorithms were developed to follow the above presentation strategy, which algorithms allow the highly efficient training of zones or areas of visual system function (and, optionally, also dysfunction or malfunction in parallel or consecutively). The detailed steps of the training procedure are described below with respect to stimulating specific areas or zones of the human visual system by optical stimuli.

During the training step, changes in the characteristics of the visual system of the human trained are recorded. In other words: The performance of the person trained in view of visually recognizing the optical stimuli presented and himself/herself presenting the desired reaction on said visual recognition step is recorded by the system/device of the present invention. To give just one example: The reaction time of the trained person on an optical stimulus presented to the intact zone of his/her visual system is measured, and the time elapsed between the emission of the optical stimulus and the reaction given (for example by pressing a button of the device), relative to an average time value measured before for the trained person as a base line value, is taken as the performance of the person with respect to the trained area of the intact zone. However, this example is not to be considered as limiting the invention; any other appropriate step may be taken, too, in order to continuously or intermittently record changes in the characteristics of the human's visual system.

In a preferred embodiment of the invention, the reaction of the person to be trained upon the presentation of one stimulus or several or many stimuli is measured, and the performance of the person is rewarded. This may happen in a way that reward points are added to a "reward account" when the responses fulfil a predetermined criterion. For example, when the person to be trained is instructed to perform as fast as possible, reward points are added to the reward account only in those cases where the response is recorded within a predetermined time delay (reaction time). Alternatively, reward points could be assigned to the reward account when a discrimination is properly made (e.g. correct form; correct colour; time discrimination).

Based on the continuous recordal of the changes in the characteristics as decribed above, the location and definition of the intact zone is adapted to said changes. This may also be conducted continuously or intermittently. In a preferred embodiment of the invention, the number of reward points is used to automatically increase the difficulty of the next task. In this way, a means to increase the training difficulty is provided, depending upon the recordal of the reaction/response shown by the person to be trained. In other words: Depending upon the performance of the trained person in processing the presented optical stimuli by the visual system, the intact visual zone is newly defined. Without wanting to be bound by the explanation, it can be assumed that, due to the effective training of the defined intact visual zone, the vision of the trained person is improved in said intact vision zone, specifically, and in general, for example by improving any function of the visual system (e.g. peripheral vision, visual acuity, ability to discriminate between different colours, shapes, movement; reduction of squinting; increase of the visual angle) or improving visual functions in general or removing partial visual system injuries. As a result thereof, the intact vision zone is enlarged or at least improved with respect to its contribution to the person's vision. As found in practice, the person to be trained experienced an improvement of the overall vision subjectively and due to a better performance in the training.

By reiterating the above-described steps, the human's intact visual field is continuously extended into zones which were previously located and defined to be transition zones Training was carried out with a personal computer for use at home where persons to be trained practised on a regular basis. The preferred embodiment of the present invention is daily training for 1 h in a darkened room for an extended time period, as for example a 6-months period as employed in this test. However, any other training period may also prove efficacious.

As the prior art devices have been inefficient, a special algorithm was developed which produced on a monitor an emission of light stimuli effecting a repetitive visual stimulation of the intact visual zone located adjacent to a transition zone and a damaged visual field sector of the human to be trained. In a first step, the "intact vision zone" was located, defined and characterized, i.e. there occured a determination of the exact visual function in said intact vision zone with respect to location, size and kind.

After said first step, there was defined a training area which is located within said intact vision zone. Said training area is a region within the intact vision zone where a regeneration of the neuronal structures of the person's visual system could be expected due to the results of the definition and characterization of the intact vision zone in the first step, e.g. due to the presence of a certain number of remaining neuronal structures.

In a subsequent step, there was conducted a stimulation of the area of intact vision based on the performance determined in the first and second steps. This approach is highly efficient because it does stimulate intact areas of the visual field.

Also, unlike prior art devices in which the program only stores the data for a later analysis, the present invention adapts, on a continuous or intermittent basis, training algorithms to the visual system performance in or near the areas of intact vision functions.

In addition, daily therapy results can be stored on suitable storing media like a tape or a disc which permits monitoring of compliance and which allows the therapy strategy to be adapted to the progress of the person.

The invention is hereinafter described in detail with reference to the Figures. While the description of the invention mainly relates to a training of persons whose visual system is severely damaged, all details of the invention, i.e. the process and the apparatus, can be applied mutatis mutandis by a skilled person to the training of persons whose visual system deteriorates smoothly due to an ageing of said person and also to persons whose regular vision is to be trained in order to maintain the quality of the vision on a high level. Insofar, the description of the training procedure in connection to persons with a severely damaged visual system, but having intact vision areas is not to be construed as a limitation of the invention. In the Figures, FIG. 1 shows the case of visual field training in a normal case where the intact vision zone has been defined to have a circular shape at least covering or even overlapping the field of the monitor frame where the target stimulus is presented. The fixation point for fixing the eyes of the person to be trained is presented in the middle of the intact vision zone, as is the target stimulus to be recognized by the person.

Figure 2:
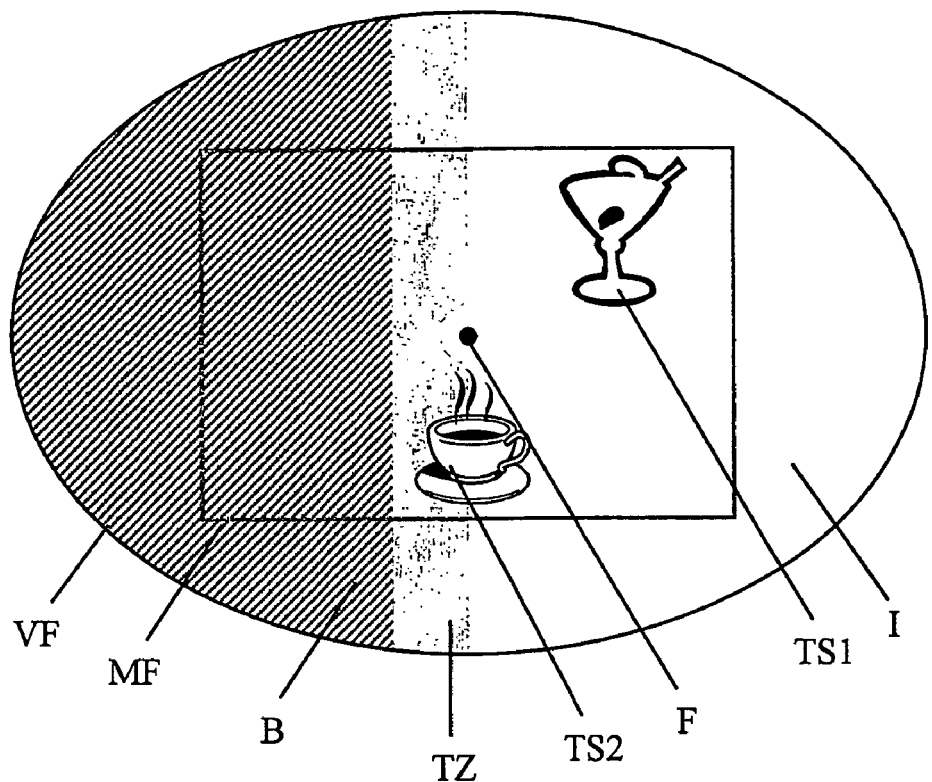

FIG. 2 shows the case where the visual system in one hemisphere does not function; the fixation point is presented in the intact vision zone, as is the target stimulus "TS1", i.e. the stimulus training the intact vision field, while another target stimulus "TS2" is presented partly in the intact and partly in the injured field, independently.

Figure 3:
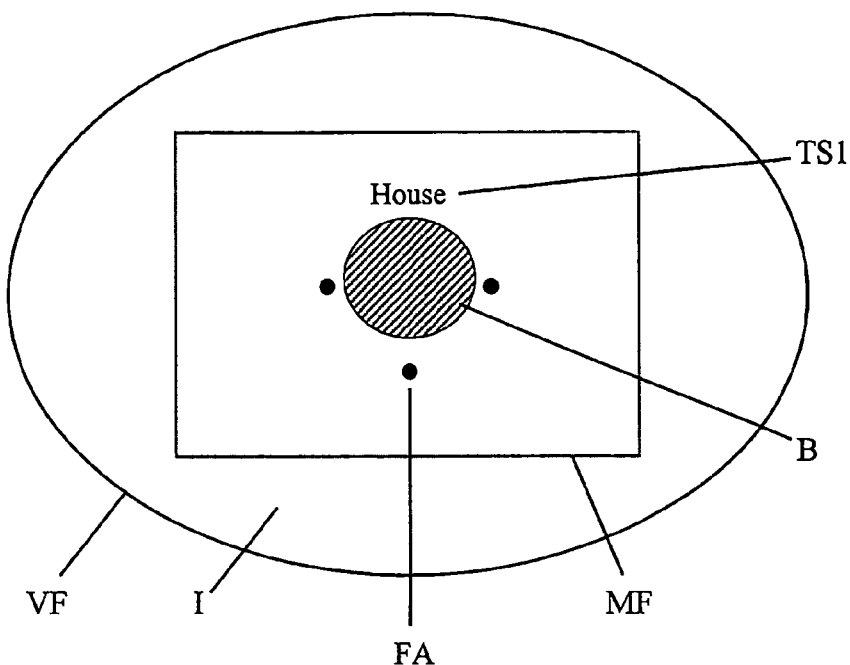

FIG. 3 shows the case where the central area of the visual system (e.g. where the fovea is located) is injured ("donut-shaped visual feld"). In such a case, the fixation point cannot be presented in the central area (due to the injury, it would not be recognized), but so-called "fixation ankers" are presented in the peripheral part of the blind region where the intact vision zone is located and defined. Then, a visual stimulus is presented in the intact vision zone, in this case in the form of a word.

FIG. 4 shows the case of a presentation of two stimuli in sequence (T1 and thereafter T2). In the same way as in FIG. 2, the visual field is intact in one part (I=intact visual field sector) and partially blind in another part (B=blind region). A priming stimulus (P) is preceeding the target stimulus (TS1) in order to increase the probability of detecting and recognizing the target.

FIG. 5 shows another case of a presentation of two stimuli in sequence (T1 and thereafter T2). In the same way as in FIG. 2, the visual field is intact in one sector (I=intact visual field sector) and partially blind in another sector (B=blind region). One of two priming stimuli P1 and P2 is presented to the person to be trained, and thereafter, one target stimulus (TS1) is presented to the intact zone of the visual field. The person will have to respond by discriminating whether a target stimulus were presented to the intact vision field in the area of the priming stimulus.

The invention is explained in further detail with reference to the Figures and the preferred embodiments of Examples 1 to 5 without being restricted to these preferred embodiments.

The computer algorithms for the step of presenting visual stimuli to the human's visual system are such that the monitor presents a fixation point, which can be presented in any part of the monitor. The fixation point serves to a fixation of the person's view to a certain point in order to allow an adjustment of the person's angle of view. In succession, additional visual stimuli are presented in or immediately adjacent to the intact vision zone, the location of which is determined in the previous step and changed in accordance with the person's performance. In the prior art device published by Kasten et al., the visual stimuli were presented independent of the persons' actual progress and were therefore inefficient and laborious. In contrast thereto, the visual stimuli are presented in the present invention perdominantly in or adjacent to the intact vision zone, i.e. an area with almost no or only slight visual system injury or deteriorated vision.

EXAMPLE 1

One preferred embodiment is intended for persons to be trained having a damage of the brain's visual system. For example, when the visual system in one hemisphere does not function, the opposite sector of the visual field is lost ("hemianopsia"); see FIG. 2. In this case, the device of the present invention would present target stimuli only in the intact vision field and not in the deficient half field. Depending upon responses to the presentation of the stimuli, increasingly more difficult target stimuli are selected to which the person to be trained has to respond until no further progress in performance can be achieved.

EXAMPLE 2

Another embodiment of the invention is useful in cases where the central area of the visual system, where the fovea is located, is injured; see FIG. 3. This may occur after retinal damages such as age-related macular degeneration. The person to be trained sees little of nothing centrally, but has a donut-like visual field with no vision in the centre but intact vision in the peripheral part of the visual system. The device of the present invention generates target stimuli (in this case letters or words) in the intact vision zone near the visual field border, i.e. above or below the damaged region and positioned near the border. The letters or words may be stationary or moving, depending, e.g. upon the difficulty of the response requested.

EXAMPLE 3

In another embodiment of the present invention (exemplified in FIG. 4), a target stimulus is preceeded by a priming stimulus. This could be a priming stimulus with an emotional content (e.g. a "Smiley" or "Happy Face"), which preceeding priming stimulus could increase the probability of detecting the subsequent target stimulus. Both stimuli are presented to the intact vision zone of the person to be trained. In one embodiment, the priming stimulus could be presented in a very short time so that it cannot be seen consciously by the person to be trained. The person would not be asked to respond to the priming stimulus. As could be found, the presentation of a priming stimulus influences the person's ability of detection of the target stimulus.

EXAMPLE 4

Another embodiment of the invention is directed to a case where two target stimuli are presented either in rapid succession or simultaneously. The response requested from the person to be trained is a discrimination whether one or several target stimuli were presented. The person would receive award points only when the discrimination problem was responded to correctly.

EXAMPLE 5

In yet another embodiment of the invention, reward points are entered into the training person's reward account only for responses which fulfil a predetermined criterion. For example, reward points could be given only if a response is recorded by the computer within a predetermined reaction time or following the correct response to a discrimination task. Preferably, the target stimulus/stimuli is/are presented to the intact vision zone, although a simultaneous or consecutive presentation of one or more than one stimulus/stimuli to the intact vision zone and the transition zone may be possible and also in the frame of the present invention.

EXAMPLE 6

In another preferred embodiment of the invention (see FIG. 5), the priming stimulus (P1, P2) may be an attention cue such as a window frame or another object which is located at the identical position as the subsequent target stimulus (TS1) presented to the intact vision zone. In this case (or also other cases), the fixation point (F in FIG. 5) may be presented to the intact vision zone or the transition zone, i.e. in a zone where the person to be trained has at least sufficient vision capability to recognize the fixation point for a fixation of his eyes.

It should be apparent from this disclosure that it is beneficial to limit the area of training to those parts in the visual field which are almost not or only slightly partially injured or deteriorated. Of course, the actual stimulus presented can vary in size, luminance, shape or color and it can be presented by various means, such as a projection screen, a simple computer monitor or other visual projection devices such as virtual reality gargles or helmet. The type of stimulus as well as the way by which it is presented is not limited, as long as it is acertained that the location of the stimulus presentation is adapted to the persons' individual deficit and as long as the majority of the stimulus presentations are given in "intact vision zones", i.e. areas having almost no or only slight impaired visual functions.

The invention claimed is:

1. A method for treating the visual system of a human, the method comprising:
    locating a first zone of intact vision within the human's visual system;
    defining a treatment area which is located within the first zone of intact vision;
    presenting visual stimuli to the treatment area
    recording changes in characteristics of the human's visual system;
    adapting the treatment area, according to the changes; and
    iterating the at least the presenting, recording and adapting so as to improve the human's overall visual system.

2. The method of claim 1, wherein the treatment area includes an additional zone selected from the group consisting of a zone of deteriorated vision, a zone of residual vision, a zone of partial vision function, and a zone of partial visual function injury.

3. The method of claim 1, wherein the size, location and kind of said treatment area are selected in accordance with the size, location and kind at least one of the first zone of intact vision, zone of partial visual system injury, zone of residual visual function and zone of visual deficit of said human.

4. The method of claim 1, wherein the visual stimuli are light stimuli.

5. The method of claim 4, wherein the light stimuli are light stimuli of at least one of different color, luminance, intensity, and shape.

6. The method of claim 1, wherein the step of presenting visual stimuli comprises presenting at least one fixation point to the humane's visual field allowing a control of the human's angle of view.

7. A method according to claim 6, further comprising presenting at least two fixation points.

8. A method according to claim 6, further comprising presenting at least three fixation points.

9. The method of claim 1, wherein substantially all visual stimuli are presented to the human's visual system in or immediately adjacent to the first zone of intact vision.

10. The method of claim 1, wherein the visual stimuli are presented on a screen.

11. The method of claim 10, wherein the screen is selected from the group consisting of a computer screen, a video screen, and a projection screen.

12. The method of claim 1, wherein the step of presenting visual stimuli is conducted on a visual projection device.

13. The method of claim 12, where in the visual projection device includes one of a virtual reality goggles and a helmet.

14. The method of claim 1, wherein the recording of changes in the characteristics of the humane's visual system comprises a recording of at least one of responsiveness, color recognition, shape recognition, and localization of the visual stimuli by the human.

15. The method of claim 1, wherein the steps of locating, defining, presenting, recording, adapting and iterating are controlled by a central data processing means.

16. The method of claim 1, wherein the step of recording includes recording changes in the human's ability to react on time-connected signal discrimination.

17. The method of claim 16, further comprising recording changes in a parameter selected from the group consisting of the human's reaction time after appearance of a stimulus, the human's ability to estimate time intervals between the appearance of two stimuli, and the human's ability to discriminate time-connected patterns of stimuli.

18. The method of claim 1, wherein the human's visual system is the visual system of a humans operator of at least one of technical machines, weapon systems, land vehicles, water vehicles and air vehicles.

19. The method of claim 1, wherein the human's visual system has been injured by one of a stroke and a trauma.

20. The method of claim 1, wherein the human is one of shortsighted and farsighted.

21. The method of claim 1, wherein the human is a child.

22. The method of claim 21, wherein the child is a squinting children.

23. The method of claim 1, wherein the human has experienced a partial visual system injury.

24. The method of claim 1, wherein the human is normal-sighted.

25. A method according to claim 1, further comprising:
   locating a second zone of intact vision within the human's visual system;
   defining a treatment area which is located, at least in part, within the second zone of intact vision;
   presenting visual stimuli to the treatment area
   recording changes in characteristics of the human's visual system;
   adapting the treatment area, according to the changes; and
   iterating at least the adapting so as to improve the human's overall visual system.

26. A method according to claim 25, wherein the first zone of intact vision and the second zone of intact vision are discontinuous.

27. A method according to claim 1, wherein the visual stimuli are selected from the group consisting of articles of daily life, letters, ciphers, words, or sentences.

28. A method according to claim 1, wherein the visual stimuli include a series of light stimuli displayed in a sequence.

29. A method according to claim 28, wherein the series of light stimuli generate the impression of a moving object.

30. A method according to claim 1, further comprising presenting a priming stimulus.

31. A method according to claim 30, wherein the priming stimulus is presented in the same position as a subsequent stimulus.

32. A method according to claim 30, wherein the priming stimulus is presented for a period of time that is too brief for conscious vision.

33. A method according to claim 30, wherein the priming stimulus is one of a smiley, a happy face, and a frame.

34. A method according to claim 1, further comprising comparing adding points to a reward account.

35. A system for treating the vision of a patient, the system comprising:
   a storage device;
   a display;
   a user input device; and
   a processor programmed to locate a zone of intact vision within a representation of a human's visual system maintained in the storage device, define a treatment area which is located within the zone of intact vision, actuate the display to present visual stimuli to the treatment area, utilize input from the user input device to record changes in characteristics of the human's visual system, and adapt the treatment area according to the changes so as to improve the human's overall visual system.

36. A system according to claim 35, wherein the processor is programmed to reiterate the actuating, utilizing, and adapting.

37. A computer program product for use on a computer system for treating the visual system of a patient, the computer program product comprising a computer usable medium having computer readable program code thereon, the computer readable program code including:
   a. a database including a representation of the visual system of the patient;
   b. program code for defining a treatment area location within a zone of intact vision of the visual system of the patient;
   c. a routine for actuating a display to present visual stimuli to the treatment area;
   d. program code for recording within the database changes in characteristics of the visual system of the patient on the basis of user input; and
   e. program code for adapting the treatment area on the basis of the changes in characteristics of the visual system.

* * * * *

UNITED STATES PATENT AND TRADEMARK OFFICE
CERTIFICATE OF CORRECTION

PATENT NO. : 7,367,671 B2
APPLICATION NO. : 10/503869
DATED : May 6, 2008
INVENTOR(S) : Bernhard Sabel Page 1 of 2

It is certified that error appears in the above-identified patent and that said Letters Patent is hereby corrected as shown below:

Title page 1, Item [54] Title of Invention
 replace "Training"
 with --Treatment--

In Col. 12, Line 4
 replace "gargles"
 with --goggles--

In Col. 12, Line 6
 replace "acertained"
 with --ascertained--

In Col. 12, Line 42 Claim 6
 replace "humane's"
 with --human's--

In Col. 12, Line 61 Claim 14
 replace "humane's"
 with --human's--

In Col. 13, Line 11 Claim 18
 replace "humans"
 with --human--

UNITED STATES PATENT AND TRADEMARK OFFICE
CERTIFICATE OF CORRECTION

PATENT NO. : 7,367,671 B2
APPLICATION NO. : 10/503869
DATED : May 6, 2008
INVENTOR(S) : Bernhard Sabel It is certified that error appears in the above-identified patent and that said Letters Patent is hereby corrected as shown below:

In Col. 13, Line 20 Claim 22
 replace "children"
 with --child--

Signed and Sealed this

Fifteenth Day of July, 2008

JON W. DUDAS
*Director of the United States Patent and Trademark Office*